(12) United States Patent
Croze et al.

(10) Patent No.: US 7,138,379 B2
(45) Date of Patent: Nov. 21, 2006

(54) USE OF THE INTERFERON RECEPTOR 2C POLYPEPTIDE CHAIN TO ENHANCE THE ANTI-GROWTH EFFECTS OF TYPE I INTERFERONS

(75) Inventors: Ed Croze, Lafayette, CA (US); David Vogel, Richmond, CA (US); Dean Russell-Harde, Oakland, CA (US)

(73) Assignee: Schering Aktiengesellschaft, Berlin (DE)

( * ) Notice: Subject to any disclaimer, the term of this patent is extended or adjusted under 35 U.S.C. 154(b) by 206 days.

(21) Appl. No.: 09/912,252

(22) Filed: Jul. 25, 2001

(65) Prior Publication Data

US 2002/0045593 A1 Apr. 18, 2002

Related U.S. Application Data

(60) Provisional application No. 60/220,844, filed on Jul. 26, 2000.

(51) Int. Cl.
*A61K 31/70* (2006.01)
*A61K 38/21* (2006.01)
*A61K 48/00* (2006.01)
*A61K 38/16* (2006.01)

(52) U.S. Cl. .................. 514/44; 424/85.4; 424/93.2

(58) Field of Classification Search .............. 514/44; 435/456, 320.1, 455
See application file for complete search history.

(56) References Cited

FOREIGN PATENT DOCUMENTS

| WO | WO 96/18413 A1 | 6/1996 |
| WO | WO 99/32141 A | 7/1999 |
| WO | WO 99/47178 A | 9/1999 |

OTHER PUBLICATIONS

Xu et al. Clin. Cancer Res. 7:3314-3324, 2001.*
Romano et al. Stem Cells 18:19-39, 2000.*
Dang et al. Clin. Cancer Res. 5:471-474, 1999.*
Verma et al. Nature 389:239-242, 1997.*
Domanski et al. J. Biol. Chem. 273:3144-3147, 1998.*
Lutfalla et al. EMBO J. 14:5100-5108, 1995.*
Fish et al., Biochemical and Biophysical Research Communications, vol. 112, No. 2, Apr. 29, 1983, "Human Leukocyte Interferon Subtypes Have Different Antiproliferative And Antiviral Activities on Human Cells".
Luis M. De La Maza, Infection and Immunity, Mar. 1985, vol. 47, No. 3, pp. 719-722, "Interferon-Induced Inhibition of *Chlamydia trachomatis*: Dissociation from Antiviral and Antiproliferative Effects".
Aye-Aye Khine, J. Of Cellular Physiology (2000) vol. 182, pp. 97-108, "Functional Significance of Globotriaosyl Ceramide in Interferon $\partial_2$/Type 1 Interferon Receptor-Mediated Antiviral Activity".
Hiroomi Tada et al., The Journal of Clinical Investigation, Jul. 2001 vol. 108, No. 1, pp. 83-95, "Systemic IFN-β gene therapy results in long-term survival in mice with established colorectal liver metastases".
Guangwen Cao et al., Cancer Gene Therapy, vol. 8 No. 7 (2001), pp. 497-505, "Adenovirus-mediated interferon-β gene therapy suppresses growth and metastasis of human prostate cancer in nude mice".
Mandell R. et al., American Association for Cancer Research, vol. 38, Mar. 1, 1997 p. 381 XP002074718, "Gene Therapy of Cancer by Retroviral Transfer and Expression of the rat sodium.iodine symporter (NIS)".
Kim, S.H. et al., An International Journal On Genes And Genomes, Sep. 1, 1997, vol. 196, No. 1-2 pp. 279-286 XP004126355, "Mammalian type I interferon receptors consists of two subunits".
Russell-Harde Dean et al., Journal of Biological Chemistry, (1995) vol. 270, No. 44, pp. 26033-26036 XP002184662 "Reconstitution of a high affinity binding site for type I interferons".
Pfeffer Lawerence M. et al., (1997), vol. 272, No. 17, pp. 11002-1105, XP002184663, "The short form of the interferon alpha/beta receptor chain 2 acts as a dominant negative for type I interferon action".

* cited by examiner

*Primary Examiner*—Quang Nguyen
(74) *Attorney, Agent, or Firm*—Berlex, Inc.

(57) ABSTRACT

The present invention is directed towards a method of potentiating the anti-growth effects of type I interferon (IFN) on cells in a target cell population comprising increasing the number of functional IFNAR2c receptors on the surface of modified cells within the target cell population and then exposing the modified cells to a therapeutically effective amount of a type I IFN or by exposure to endogenously produced IFN.

8 Claims, 10 Drawing Sheets

HTbetaL.2 cells

MDA231 cells

MDA231 cells phase-contrast TUNEL

A

B

C

D

E

F

SEQUENCE LISTING

```
<160> NUMBER OF SEQ ID NOS: 4

<210> SEQ ID NO 1
<211> LENGTH: 513
<212> TYPE: PRT
<213> ORGANISM: Murine sp.

<400> SEQUENCE: 1

Met Arg Ser Arg Cys Thr Val Ser Ala Val Gly Leu Leu Ser Leu Cys
  1               5                  10                  15

Leu Val Val Ser Ala Ser Leu Glu Thr Ile Thr Pro Ser Ala Phe Asp
             20                  25                  30

Gly Tyr Pro Asp Glu Pro Cys Thr Ile Asn Ile Thr Ile Arg Asn Ser
         35                  40                  45

Arg Leu Ile Leu Ser Trp Glu Leu Glu Asn Lys Ser Gly Pro Pro Ala
     50                  55                  60

Asn Tyr Thr Leu Trp Tyr Thr Val Met Ser Lys Asp Glu Asn Leu Thr
 65                  70                  75                  80

Lys Val Lys Asn Cys Ser Asp Thr Thr Lys Ser Ser Cys Asp Val Thr
                 85                  90                  95

Asp Lys Trp Leu Glu Gly Met Glu Ser Tyr Val Val Ala Ile Val Ile
            100                 105                 110

Val His Arg Gly Asp Leu Thr Val Cys Arg Cys Ser Asp Tyr Ile Val
        115                 120                 125

Pro Ala Asn Ala Pro Leu Glu Pro Pro Glu Phe Glu Ile Val Gly Phe
    130                 135                 140

Thr Asp His Ile Asn Val Thr Met Glu Phe Pro Pro Val Thr Ser Lys
145                 150                 155                 160

Ile Ile Gln Glu Lys Met Lys Thr Thr Pro Phe Val Ile Lys Glu Gln
                165                 170                 175
```

-continued

Ile Gly Asp Ser Val Arg Lys Lys His Glu Pro Lys Val Asn Asn Val
            180                 185                 190

Thr Gly Asn Phe Thr Phe Val Leu Arg Asp Leu Leu Pro Lys Thr Asn
            195                 200                 205

Tyr Cys Val Ser Leu Tyr Phe Asp Asp Pro Ala Ile Lys Ser Pro
            210                 215                 220

Leu Lys Cys Ile Val Leu Gln Pro Gly Gln Ser Gly Leu Ser Glu
225                 230                 235                 240

Ser Ala Ile Val Gly Ile Thr Thr Ser Cys Leu Val Met Val Phe
                245                 250                 255

Val Ser Thr Ile Val Met Leu Lys Arg Ile Gly Tyr Ile Cys Leu Lys
            260                 265                 270

Asp Asn Leu Pro Asn Val Leu Asn Phe Arg His Phe Leu Thr Trp Ile
            275                 280                 285

Ile Pro Glu Arg Ser Pro Ser Glu Ala Ile Asp Arg Leu Glu Ile Ile
            290                 295                 300

Pro Thr Asn Lys Lys Arg Leu Trp Asn Tyr Asp Tyr Glu Asp Gly
305                 310                 315                 320

Ser Asp Ser Asp Glu Glu Val Pro Thr Ala Ser Val Thr Gly Tyr Thr
                325                 330                 335

Met His Glu Leu Thr Gly Lys Pro Leu Gln Gln Thr Ser Asp Thr Ser
            340                 345                 350

Ala Ser Pro Glu Asp Pro Leu His Glu Glu Asp Ser Gly Ala Glu Glu
            355                 360                 365

Ser Asp Glu Ala Gly Ala Gly Ala Gly Ala Glu Pro Glu Leu Pro Thr
370                 375                 380

Glu Ala Gly Ala Gly Pro Ser Glu Asp Pro Thr Gly Pro Tyr Glu Arg
385                 390                 395                 400

Arg Lys Ser Val Leu Glu Asp Ser Phe Pro Arg Glu Asp Asn Ser Ser
                405                 410                 415

Met Asp Glu Pro Gly Asp Asn Ile Ile Phe Asn Val Ser Leu Asn Ser
            420                 425                 430

Val Phe Leu Arg Val Leu His Asp Glu Asp Ala Ser Glu Thr Leu Ser
            435                 440                 445

Leu Glu Glu Asp Thr Ile Leu Leu Asp Glu Gly Pro Gln Arg Thr Glu
            450                 455                 460

Ser Asp Leu Arg Ile Ala Gly Gly Asp Arg Thr Gln Pro Pro Leu Pro
465                 470                 475                 480

Ser Leu Pro Ser Gln Asp Leu Trp Thr Glu Asp Gly Ser Ser Glu Lys
                485                 490                 495

Ser Asp Thr Ser Asp Ser Asp Ala Asp Val Gly Asp Gly Tyr Ile Met
            500                 505                 510

Arg

<210> SEQ ID NO 2
<211> LENGTH: 2468
<212> TYPE: DNA
<213> ORGANISM: Murine sp.

<400> SEQUENCE: 2
cgtgaacaga gaacgaggcg agaggcccca ggacatccca gaggggggatt cacgagaccc    60 ggcgattcag gtgtgagagc agaaaaacgg acttaagagc tgagcaggat gcgttcacgg    120
tgcaccgtct ctgccgtcgg tctcctcagc ttgtgtcttg tggtgtctgc gagcctagag    180

-continued

```
actatcacac cgtctgcttt tgatgggtat ccagatgaac cttgcactat aaacataaca      240
atacgaaatt cccggctaat tttatcctgg gaattagaga acaagtctgg cccacccgct      300
aactacaccc tctggtacac agtcatgagc aaagacgaaa atctgacgaa ggttaagaac      360
tgttcagata ccacgaagtc atcatgtgac gtgacagata agtggttgga gggcatggag      420
agctacgtcg tcgccatcgt catagtgcac agagggact tgaccgtgtg ccgctgctca       480
gactacatcg tgcctgcaaa cgctcctctt gagccgccag aatttgagat cgttggcttt      540
acagaccaca taaacgtgac gatggaattt ccacctgtca cttccaaaat aatccaggaa      600
aagatgaaga ctacacccttt tgtcatcaaa gaacagatag gggacagcgt taggaagaag     660
cacgagccca aagtgaataa tgtcactggg aacttcacat ttgtccttag agacttactt     720
ccaaagacaa actactgtgt atctctttat tttgatgatg accccgcaat aaaatctccc     780
ttaaaatgca tcgtccttca gcctggccag gaatcaggat tatcagaatc tgctatagta    840
ggaataacta cttcgtgttt ggtagtgatg gttttcgtga gcactatcgt aatgctgaaa    900
cggattggtt atatatgcct aaaagacaat ttgcccaatg tcttgaactt ccgccacttt    960
ttaacctgga taatccctga acggtcacct tcagaagcca tcgatcggct ggaaatcatc   1020
cccacaaaca agaagaagag actgtggaat tacgattatg aggatggcag tgacagtgac   1080
gaagaggtcc ccacagcaag tgtcactggc tacaccatgc atgaactgac gggcaagcct   1140
ctgcaacaaa cctctgacac ctcagccagc cccgaggatc ccctgcatga agaagattca   1200
ggcgctgagg aatctgatga agctggagca ggggctggag ctgagccaga actccccaca   1260
gaggcggggg cggggccttc agaagacccc actggcccct atgagagaag aaagagtgtg   1320
ctcgaggact cattccccag ggaggacaac agctccatgg atgagcctgg ggacaacatt   1380
atcttcaacg tgagcttaaa ctctgtgttt ctgagggttc tccatgatga agatgcctca   1440
gagacattat ctctcgaaga agacaccatc ctcctagacg aaggtcccca gaggacagag   1500
tcagaccttc ggatagctgg tggggacagg acacagccgc cctccccagc cttccttccc   1560
aggatctatg gactgaagat gggtcatctg agaaatcaga cacctcagat tccgatgctg   1620
atgtggggga cggctacatc atgagatgac tccaaagggg ttcactgact ggcgctgggc   1680
acctacaggg tttctcttca gagtccgact tgatgccttg tggtctccag gtgtctgtca   1740
tggagggact agagaactct acagccctct tggcccttgc tgattggcct tctctatgca   1800
gattgacaat ttgggcatca ggattgttta caggggtcat gagcgtgatc tgcccacccc   1860
ctttccacta atgcactaag gtggtttgtg ttacatttcc cagggaacag gttcagtgtg   1920
ttttcagagg cagcccaagg tctcctatcc ctatgttgtt tcctaggaaa tgattaaatt   1980
gggggggagag aaagggaaag aaaaactgcc caagcagtgt tcaggaggac tccaggaatg   2040
aacctgaaag gggcggaag ggtcagaggt aaggcatgct gagctggctg ctggcacaag     2100
aaaagccatc aaggtttgag cccctgctgt ctgggccctt cccagatgtc aacatctgtc   2160
tcctctactc taggaagttc attcacccat aaagccccgc acagtgcacg tgaggagggg   2220
gagaagccgc aggaataatt ctaggatcca acgcgtgact cagagagagg gatatcatgg   2280
ccatatttta aggtcatttc tcgtcaactc tttaaccttc agtttttctca acttatgaaa   2340
taaagggact gagcaggtag gcttggggag agatgcccaa agtggatgaa gggtgtaggg   2400
tcctcccatc ttaatcttct cacccccaaac cagggtttca caattttctt cttttcaaag   2460
aaggactg                                                             2468
```

<210> SEQ ID NO 3
<211> LENGTH: 515
<212> TYPE: PRT
<213> ORGANISM: Homo sapiens

<400> SEQUENCE: 3

Met Leu Leu Ser Gln Asn Ala Phe Ile Phe Arg Ser Leu Asn Leu Val
1               5                   10                  15

Leu Met Val Tyr Ile Ser Leu Val Phe Gly Ile Ser Tyr Asp Ser Pro
            20                  25                  30

Asp Tyr Thr Asp Glu Ser Cys Thr Phe Lys Ile Ser Leu Arg Asn Phe
        35                  40                  45

Arg Ser Ile Leu Ser Trp Glu Leu Lys Asn His Ser Ile Val Pro Thr
    50                  55                  60

His Tyr Thr Leu Leu Tyr Thr Ile Met Ser Lys Pro Glu Asp Leu Lys
65                  70                  75                  80

Val Val Lys Asn Cys Ala Asn Thr Thr Arg Ser Phe Cys Asp Leu Thr
                85                  90                  95

Asp Glu Trp Arg Ser Thr His Glu Ala Tyr Val Thr Val Leu Glu Gly
            100                 105                 110

Phe Ser Gly Asn Thr Thr Leu Phe Ser Cys Ser His Asn Phe Trp Leu
        115                 120                 125

Ala Ile Asp Met Ser Phe Glu Pro Pro Glu Phe Glu Ile Val Gly Phe
    130                 135                 140

Thr Asn His Ile Asn Val Val Lys Phe Pro Ser Ile Val Glu Glu
145                 150                 155                 160

Glu Leu Gln Phe Asp Leu Ser Leu Val Ile Glu Gln Ser Glu Gly
            165                 170                 175

Ile Val Lys Lys His Lys Pro Glu Ile Lys Gly Asn Met Ser Gly Asn
        180                 185                 190

Phe Thr Tyr Ile Ile Asp Lys Leu Ile Pro Asn Thr Asn Tyr Cys Val
    195                 200                 205

Ser Val Tyr Leu Glu His Ser Asp Glu Gln Ala Val Ile Lys Ser Pro
210                 215                 220

Leu Lys Cys Thr Leu Leu Pro Pro Gly Gln Glu Ser Glu Ser Ala Glu
225                 230                 235                 240

Ser Ala Lys Ile Gly Gly Ile Ile Thr Val Phe Leu Ile Ala Leu Val
            245                 250                 255

Leu Thr Ser Thr Ile Val Thr Leu Lys Trp Ile Gly Tyr Ile Cys Leu
        260                 265                 270

Arg Asn Ser Leu Pro Lys Val Leu Asn Phe His Asn Phe Leu Ala Trp
    275                 280                 285

Pro Phe Pro Asn Leu Pro Pro Leu Glu Ala Met Asp Met Val Glu Val
290                 295                 300

Ile Tyr Ile Asn Arg Lys Lys Lys Val Trp Asp Tyr Asn Tyr Asp Asp
305                 310                 315                 320

Glu Ser Asp Ser Asp Thr Glu Ala Ala Pro Arg Thr Ser Gly Gly Gly
            325                 330                 335

Tyr Thr Met His Gly Leu Thr Val Arg Pro Leu Gly Gln Ala Ser Ala
        340                 345                 350

Thr Ser Thr Glu Ser Gln Leu Ile Asp Pro Glu Ser Glu Glu Glu Pro
    355                 360                 365

Asp Leu Pro Glu Val Asp Val Glu Leu Pro Thr Met Pro Lys Asp Ser
370                 375                 380

```
Pro Gln Gln Leu Glu Leu Leu Ser Gly Pro Cys Glu Arg Arg Lys Ser
385                 390                 395                 400

Pro Leu Gln Asp Pro Phe Pro Glu Glu Asp Tyr Ser Ser Thr Glu Gly
                405                 410                 415

Ser Gly Gly Arg Ile Thr Phe Asn Val Asp Leu Asn Ser Val Phe Leu
            420                 425                 430

Arg Val Leu Asp Asp Glu Asp Ser Asp Leu Glu Ala Pro Leu Met
            435                 440                 445

Leu Ser Ser His Leu Glu Glu Met Val Asp Pro Glu Asp Pro Asp Asn
        450                 455                 460

Val Gln Ser Asn His Leu Leu Ala Ser Gly Glu Gly Thr Gln Pro Thr
465                 470                 475                 480

Phe Pro Ser Pro Ser Glu Gly Leu Trp Ser Glu Asp Ala Pro Ser
                485                 490                 495

Asp Gln Ser Asp Thr Ser Glu Ser Asp Val Asp Leu Gly Asp Gly Tyr
            500                 505                 510

Ile Met Arg
        515

<210> SEQ ID NO 4
<211> LENGTH: 2636
<212> TYPE: DNA
<213> ORGANISM: Homo sapiens

<400> SEQUENCE: 4
```

| | | | | | |
|---|---|---|---|---|---|
| ctctaaagcg | caaggcgaga | gctgcaaaga | tgtaaaagtc | aagagaagac | tctaaaaata | 60 |
| gcaaagatgc | ttttgagcca | gaatgccttc | atcttcagat | cacttaattt | ggttctcatg | 120 |
| gtgtatatca | gcctcgtgtt | tggtatttca | tatgattcgc | ctgattacac | agatgaatct | 180 |
| tgcactttca | agatatcatt | gcgaaatttc | cggtccatct | tatcatggga | attaaaaaac | 240 |
| cactccattg | taccaactca | ctatacattg | ctgtatacaa | tcatgagtaa | accagaagat | 300 |
| ttgaaggtgg | ttaagaactg | tgcaaatacc | acaagatcat | tttgtgacct | cacagatgag | 360 |
| tggagaagca | cacgaggc | ctatgtcacc | gtcctagaag | gattcagcgg | gaacacaacg | 420 |
| ttgttcagtt | gctcacacaa | tttctggctg | gccatagaca | tgtcttttga | accaccagag | 480 |
| tttgagattg | ttggttttac | caaccacatt | aatgtggtgg | tgaaatttcc | atctattgtt | 540 |
| gaggaagaat | acagtttga | tttatctctc | gtcattgaag | aacagtcaga | gggaattgtt | 600 |
| aagaagcata | aacccgaaat | aaaaggaaac | atgagtggaa | atttcaccta | tatcattgac | 660 |
| aagttaattc | caaacacgaa | ctactgtgta | tctgtttatt | tagagcacag | tgatgagcaa | 720 |
| gcagtaataa | agtctcccttt | aaaatgcacc | ctccttccac | ctggccagga | atcagaatca | 780 |
| gcagaatctg | ccaaaatagg | aggaataatt | actgtgtttt | tgatagcatt | ggtcttgaca | 840 |
| agcaccatag | tgacactgaa | atggattggt | tatatatgct | taagaaatag | cctccccaaa | 900 |
| gtcttgaatt | ttcataactt | tttagcctgg | ccatttccta | acctgccacc | gttggaagcc | 960 |
| atggatatgg | tggaggtcat | ttacatcaac | agaaagaaga | agtgtgggga | ttataattat | 1020 |
| gatgatgaaa | gtgatagcga | tactgaggca | gcgcccagga | caagtggcgg | tggctatacc | 1080 |
| atgcatggac | tgactgtcag | gcctctgggt | caggcctctg | ccacctctac | agaatcccag | 1140 |
| ttgatagacc | cggagtccga | ggaggagcct | gacctgcctg | aggttgatgt | ggagctcccc | 1200 |
| acgatgccaa | aggacagccc | tcagcagttg | aactcttga | gtgggccctg | tgagaggaga | 1260 |
| aagagtccac | tccaggaccc | ttttcccgaa | gaggactaca | gctccacgga | ggggtctggg | 1320 |

```
ggcagaatta ccttcaatgt ggacttaaac tctgtgtttt tgagagttct tgatgacgag    1380
gacagtgacg acttagaagc ccctctgatg ctatcgtctc atctggaaga gatggttgac    1440
ccagaggatc ctgataatgt gcaatcaaac catttgctgg ccagcgggga agggacacag    1500
ccaacctttc ccagcccctc ttcagagggc ctgtggtccg aagatgctcc atctgatcaa    1560
agtgacactt ctgagtcaga tgttgacctt ggggatggtt atataatgag atgactccaa    1620
aactattgaa tgaacttgga cagacaagca cctacagggt tctttgtctc tgcatcctaa    1680
cttgctgcct tatcgtctgc aagtgttctc caagggaagg aggaggaaac tgtggtgttc    1740
ctttcttcca ggtgacatca cctatgcaca ttcccagtat ggggaccata gtatcattca    1800
gtgcattgtt tacatattca aagtggtgca ctttgaagga agcacatgtg caccttttcct   1860
ttacactaat gcacttagga tgtttctgca tcatgtctac cagggagcag ggttccccac    1920
agtttcagag gtggtccagg accctatgat atttctcttc tttcgttctt tttttttttt    1980
tttttttgaga cagagtctcg ttctgtcacc caagctggag cgcaatggtg tgatcttggc    2040
tcgctgcaac atccgcctcc cgggttcggg tgattctcct gcctcagcct ccctcgcaag    2100
tagctgggat tacaggcgcc tgccaccatg cctagcaaat ttttgtattt ttagtagaga    2160
caggattttg ccatgttggc caggctggtc tcgaactcct gacctcaagt gatctgccct    2220
cctcagcctc gtaaagtgct gggattacag gggtgagccg ctgtgcctgg ctggccctgt    2280
gatatttctg tgaaataaat tgggccaggg tgggagcagg gaaagaaaag gaaaatagta    2340
gcaagagctg caaagcaggc aggaagggag gaggagagcc aggtgagcag tggagagaag    2400
gggggccctg cacaaggaaa cagggaagag ccatcgaagt ttcagtcggt gagccttggg    2460
cacctcaccc atgtcacatc ctgtctcctg caattggaat tccaccttgt ccagccctcc    2520
ccagttaaag tggggaagac agactttagg atcacgtgtg tgactaatac agaaaggaaa    2580
catggcgtcg gggagaggga taaaacctga atgccatatt ttaagttaaa aaaaaa       2636
```

US 7,138,379 B2

USE OF THE INTERFERON RECEPTOR 2C POLYPEPTIDE CHAIN TO ENHANCE THE ANTI-GROWTH EFFECTS OF TYPE I INTERFERONS

This application claims benefit of U.S. Provisional Application No. 60/220,844, filed Jul. 26, 2000, which is incorporated by reference in its entirety.

BACKGROUND OF THE INVENTION

Since their initial discovery in 1957, interferons, originally described as factors that interfered with viral infection, have been widely studied. Interferons (IFNs) are now recognized as an integral part of the body's natural defense system, and they are used successfully as therapeutic agents for the treatment of a number of human diseases. IFNs are segregated into two classes defined as either type I or type II. Type I IFNs include a family of related proteins, IFNα, IFNβ, IFNω, IFNτ and IFNδ, whereas type II IFN consists of one protein, IFNγ, which has limited homology to type I IFNs.

Two receptor proteins, IFNAR1 and IFNAR2 are known to be involved in type I IFN binding.

DESCRIPTION OF THE INVENTION

The present invention relates to methods of potentiating the effects of effector ligands by increasing the number of functional receptors for receptor ligands on the cell surface. As used herein, increasing the number of functional receptors means any amount of expression of functional receptor in excess of the amount normally expressed by the cell. Thus, the increase may be accomplished by increasing the total number of receptor proteins on the surface of the cell or by replacing non-functional receptor protein with functional receptor protein, such as, for example, by mutagenesis. "Potentiate", as used herein, means any enhancement of the effects of the effector ligand.

In one aspect, the present invention relates to a method of potentiating the effects of an effector ligand on a target cell population comprising tumor cells by increasing the number of functional receptors for the effector ligand on the cell surface of modified cells within the target cell population and then treating the modified cells with a therapeutically effective amount of the effector ligand. As used herein, a target cell population may comprise one or more cells and modified cells within the target cell population may comprise one or more cells of the target cell population.

In another aspect, the present invention relates to a method of potentiating the effects of IFN on a target cell population by increasing the number of functional receptors for IFN on the cell surface of modified cells within the target cell population and then treating the modified cells with a therapeutically effective amount of IFN. Effects of IFN include, for example, antiviral effects, anti-growth effects, and immunoregulatory effects. For example, it has been found that increasing the expression of the IFNAR2c polypeptide on the surface of cells within a target cell population potentiates the effects of type I IFN on cells of the target population. In particular, increasing the number of functional receptors for type I IFN on the cell surface of modified cells within a target cell population can potentiate the anti-growth effects of type I IFN on the target cell population.

As used herein, anti-growth effects include anti-proliferative and apoptotic effects, as well as any other effects which result in cell death, a cessation of cell growth, or the slowing of cell growth. Anti-proliferative effects, as used herein, includes, for example, cell cycle arrest or an increase in cell cycling time, as well as the induction of inducers of apoptosis, the induction of factors negatively regulating protein synthesis, DNA synthesis, or RNA synthesis, or the activation of inhibitors of metabolic pathways.

Without wishing to be limited by any theory of the invention, the inventors believe that the type I IFN acts directly on cells with increased IFNAR2c expression to elicit these anti-growth effects. However, it is also contemplated as part of this invention that, in lieu of the direct effect or in addition to the direct effect, type I IFN may exhibit anti-growth effects via a bystander effect, wherein the type I IFN acts on the cells with increased IFNAR2c expression to elicit the secretion of a factor which has an anti-growth effect on adjacent cells.

Accordingly, the present invention relates to methods of potentiating the anti-growth effects of a type I IFN on a target cell population by increasing the number of functional IFNAR2c receptor chains expressed on the surface of modified cells within the target cell population and then treating the modified cells with a therapeutically effective amount of at least one effector ligand which binds to the type I IFN receptor. Increasing the number of functional IFNAR1 receptor chains on the surface of the cell is also contemplated as part of this invention. A preferred effector ligand which binds to the type I IFN receptor is a type I IFN.

"Modified cells", as used herein, means cells which have been modified to express increased levels of a functional receptor for an effector ligand on the cell surface. Modified cells may include cells that have been modified in vivo or ex vivo to express increased levels of the functional receptor for the receptor ligand. Modified cells which are modified ex vivo can be subsequently transferred to the target cell population after ex vivo modification. Modified cells may also include naturally occurring cells which express relatively high levels of the effector ligand receptor and which are added to the target cell population.

As used, herein, an effector ligand refers to any molecule which binds to the effector ligand receptor and which achieves at least partial activation of the effector ligand receptor. Effector ligands include, but are not limited to, naturally occurring effector ligands, modified effector ligands, chimeric effector ligands, effector ligand mimetics, or antibodies to the effector ligand receptor.

Preferred effector ligands include, for example, growth factors, cytokines, chemotactic factors, and hematopoietic factors. Particularly, preferred effector ligands include, but are not limited to, the following: IFNs; tumor necrosis factors (TNF), for example, TNFα and TNFβ; interleukins (IL), for example, IL-1, IL-2, IL-3, IL-4, IL-5, IL-6, IL-7, IL-8, IL-9, IL-10, IL-11, IL-12, and IL-13; colony stimulating factors (CSF), for example, granulocyte-macrophage-CSF (GM-CSF), monocyte-CSF (M-CSF), granulocyte-CSF (G-CSF); erythropoietin (EPO); stem cell factor (SCF); leukemia inhibitory factor (LIF); epidermal growth factor (EGF), Oncostatin M (OSM), chemokine receptor 1 or 5 (CCR1 or CCR5), etc.

A particularly preferred effector ligand is an effector ligand which binds to a type I IFN receptor, including type I IFNs. As used herein type I IFNs include IFNα, IFNβ, IFNω, IFNτ and IFNδ, or any newly defined type I IFN, all of which may be used in accordance with the invention. In accordance with the invention, the type I IFN employed may be, for example, any subtype with anti-growth activity, antiviral activity, or immunoregulatory activity. The subtype may be a naturally occurring or a recombinant subtype, including hybrids of two or more subtypes, or analogs thereof. Anti-growth activity may be determined by any techniques that are well known in the art, including those described in the examples below. *Methods in Enzymology*, Vol. 119, ed. Sidney Pestka. A type I IFN used in accordance with this invention preferably has an anti-growth activity such that thymidine incorporation in HT1080 cells is inhibited by 5%, preferably 10%, more preferably 15% after incubation for 24 hours in an optimal concentration of the IFN. Mixtures of different subtypes may also be used. Preferably, the type I IFNs that may be used in accordance with this invention include IFNα and IFNβ, including but not limited to the following: IFNβ subtypes, including but not limited to IFNβ1b and IFNβ1a; IFNα subtypes including but not limited to IFNα2, IFNα5, IFNα13, IFNα6, IFNα14, IFNα16, IFNα21, IFNα10, IFNα46, IFNα46, IFNα7, and consensus alpha IFNs. Examples of IFNs that may be used in conjunction with the invention include but are not limited to the following. For IFNβ1b, "Betaseron", a recombinantly produced human IFNβ, wherein the cysteine residue at the 17 position has been replaced by serine, as disclosed and claimed in U.S. Pat. No. 4,588,585, may be employed. Additionally, a recombinantly produced IFNβ1a, which is produced in Chinese hamster ovary (CHO) cells, may also be employed. For IFNα, human alpha-IFN products Intron® (Schering-Plough), Roferon® (Hoffinan-LaRoche) and Infergen® (Amgen) may be employed. Other IFNs which may be employed include consensus type I alpha IFNs as described, for example in U.S. Pat. Nos. 4,695,623, 4,897,471, and 5,541,293. Interferons employed as part of this invention may also be modified by conjugation to other molecules, such as described for example, in U.S. Pat. No. 5,981,709.

It is contemplated as part of this invention that the number of functional effector ligand receptors on the surface of a modified cell may be increased in a variety of different ways. For example, up-regulation of gene expression of the IFNAR2c gene may be employed to increase the number of IFNAR2c receptor proteins on the cell. Up-regulation of gene expression may be accomplished, for example, by introducing an exogenous polynucleotide encoding the IFNAR2c polypeptide into the modified cells or by positively affecting gene transcription of the endogenous IFNAR2c gene or an exogenous IFNAR2c gene in the modified cells. For example, up-regulation of gene expression may be accomplished by stimulating the promoter or other regulatory sequences, either directly or indirectly, or by activating genes which stimulate IFNAR2c polypeptide production. For example, small molecules may be employed to stimulate the promoter of the IFNAR2c gene. Small molecules that up-regulate transcription may be identified using techniques that are well known in the art. Additionally, various methods that are well known in the art may be employed to increase the stability of messenger RNA coding for the IFNAR2c protein or to increase stability of the IFNAR2c polypeptide.

A preferred method for increasing the number of functional IFNAR2c polypeptides on the surface of modified cells is by the introducing at least one exogenous polynucleotide encoding an IFNAR2c polypeptide into the modified cells. Any exogenous IFNAR2c gene may be used in accordance with the invention, including, for example, the human IFNAR2c gene or any other mammalian IFNAR2c gene such as mouse, rat, etc. The DNA sequence of a gene encoding the full-length human IFNAR2c polypeptide, and the corresponding amino acid sequence, are described in Lutfalla et al., 1995, *EMBO J.* 14(20):5100–5108; Domanski et al., 1995, *J Biol. Chem.* 270:21606–21611; and SEQ ID NOS. 3 and 4, filed herewith. The DNA sequence of a gene encoding the full-length murine IFNAR2c polypeptide, and the corresponding amino acid sequence are shown in Owczarek et al., 1997, *J. Biol. Chem.* 272:23865–23870 and SEQ ID NOS. 1 and 2, filed herewith. A partial DNA sequence of the gene encoding the human IFNAR2c polypeptide are also disclosed in Novick, U.S. Pat. No. 5,821,078, EP 0 588 177 A2, and EP 0676 413 A2. As used herein, an exogenous IFNAR2c gene refers to any IFNAR2c gene which is added to the cells, including the addition to the cell of another copy of any endogenous IFNAR2c gene.

The invention relates not only to increasing the number of naturally occurring IFNAR2c polypeptides on the surface of a target cell, but also to increasing the number of mutant IFNAR2c polypeptides on the surface of a cell. For example, changes in the amino acid sequence of IFNAR2c are contemplated in the present invention. The IFNAR2c polypeptide can be altered by changing the DNA encoding the protein. Conservative amino acid sequence alterations are preferred, using amino acids that have the same or similar properties. Illustrative amino acid substitutions include the following changes: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine, glutamine, or glutamate; methionine to leucine or isoleucine; phenylalanine to tyrosine, leucine or methionine; serine to threonine; threonine to serine; tryptophan to tyrosine; tyrosine to tryptophan or phenylalanine; valine to isoleucine or leucine.

Polynucleotide sequences of the invention include DNA, cDNA and RNA sequences which encode IFNAR2c polypeptides. Such polynucleotides include naturally occurring, synthetic, and intentionally manipulated polynucleotides. For example, portions of the mRNA sequence may be altered due to alternate RNA splicing patterns or the use of alternate promoters for RNA transcription. As another example, IFNAR2c polynucleotides may be subjected to site-directed mutagenesis. The invention includes any polynucleotide encoding an IFNAR2c polypeptide having biological activity. Biological activity of an IFNAR2c polypeptide, as used herein, refers to a polypeptide which, when expressed on the surface of a cell, has one of the following activities: (1) binds a type I IFN; (2) is able to potentiate at least some IFN-mediated activity when dimerized with IFNAR1; (3) antibody binding activity, wherein antibodies directed against IFNAR2c inhibit or block at least one IFN-mediated activity.

Suitable target cell populations for the practice of the invention include any cell population which would benefit from a potentiation of IFN-mediated activity. For example, proliferative cell conditions may be treated in accordance with this invention. Proliferative cell condition, as used herein, includes any condition wherein it is desirable to limit cell proliferation, including cancer or neoplastic conditions. Cancer cells include but are not limited to cells involved in hairy cell leukemia, multiple myeloma, Kaposi's sarcoma, cervical neoplasia, basal cell carcinoma, squamous cell carcinoma, melanoma, renal cell carcinoma, carcinoid tumors, cutaneous T cell lymphoma, non-Hodgkins's lymphoma, head and neck tumors, and breast, lung and prostate tumors, pancreatic tumors, and adenocarcinomas. Cancer cell populations which are part of solid tumors are particularly contemplated as part of this invention. Additionally, inoperable cancers such as brain cancer, pancreatic cancer, and later stage metastatic disease are particularly contemplated as part of the invention.

Cells involved in proliferative cell conditions include cell types involved in myeloproliferative disorders. Examples of myeloproliferative disorders include, for example, chronic myelogenous leukemia, polycythaemia vera, agnogenic myeloid metaplasia and idiopathic thrombocythaemia. Proliferative cell conditions also include conditions, such as, for example, coronary restenosis. The use of type I IFNs for the treatment of coronary restenosis is described for example in U.S. Pat. No. 5,681,558.

It is also contemplated as part of this invention that the methods of this invention may be used in conjunction with the administration of other growth regulator polypeptides to the target cell population. For example, according to the methods of the invention, IFN may be administered to the target cell population containing cells modified to express increased levels of an IFNAR2c polypeptide in conjunction with the administration to the target cell population of other growth regulator polypeptides such as growth factors or cytokines, including for example interleukins. Additionally, in accordance with the invention, cells of the target cell population may be modified to express increased amounts of more than one type of effector ligand receptor, such as for example, a type I IFN receptor and an interleukin receptor, either on the same modified cells or different modified cells within a target cell population, with subsequent treatment with the corresponding effector ligands.

The present invention also provides gene therapy for the treatment of proliferative cell conditions. Such therapy would achieve its therapeutic effect, for example, by introduction of the IFNAR2c gene into modified cells of the target cell population, followed by treatment of the modified cells with a type I IFN or any other effective ligand to the IFN receptor. The ligand to the IFN receptor may be added exogenously or produced endogenously. The IFNAR2c gene may be delivered to the organism in any effective manner, e.g. using a vector or other delivery vehicle, or as naked DNA. DNA delivery vehicles can include viral vectors such as adenoviruses, adeno-associated viruses, and retroviral vectors. See, for example: Bilbao et al., 1998, *Tumor Targeting* 3:59–79; Yia-Herttuala and Martin, 2000, *Lancet* 355:213–222; Chu et al., 1994, *Gene Therapy* 1:292–299; Couture et al., 1994, *Human Gene Therapy* 5:667–677; Eiverhand et al., 1995, *Gene Therapy* 2:336–343. Non-viral vectors which are also suitable include DNA-lipid complexes, for example liposome mediated or ligand/poly-L-lysine conjugates, such as asialoglyco-protein-mediated delivery systems. See, for example: Feigner et al., 1994, *J. Biol. Chem.* 269:2550–2561; Derossi et al., 1995, *Restor. Neurol. Neuros.* 8:7–10; and Abcallah et al., 1995, *Biol. Cell* 85:1–7. Retroviruses from which the retroviral vectors may be derived include but are not limited to Moloney murine leukemia virus (MoMuLV), Harvey murine sarcoma virus (HaMuSV), murine mammary tumor virus (MuMTV), and Rous Sarcoma Virus (RSV). It is also contemplated as part of this invention that the ligand, or a gene encoding the ligand, may be included in the gene therapy delivery vehicle along with the gene encoding the IFNAR2c polypeptide.

The vector is administered to the host either locally or systemically. Typically, the vector is administered systemically by intravenous injection. Suitable viral titers will depend on a number of factors, such as the particular vector chosen, the host, the mode of administration, the strength of the promoter used, and the severity of the disease being treated. For mice, an adenovirus vector is preferably administered as an injection at a dose range of from about $5.0 \times 10^6$ to about $10 \times 10^6$ plaque forming units (PFU) per gram body weight. Preferred dosages range from at least about $6-9 \times 10^6$ PFU per gram of body weight, and more preferred is from at least about $6.7-8.6 \times 10^6$ PFU per gram of body weight.

Animals which contain modified cells that express increased levels of the IFNAR2c gene are useful models for studying the effect of type I IFN on target cell populations that contain the modified cells. This invention is specifically directed to gene therapy in humans. Also contemplated as part of this invention is the use of gene therapy in animals, including household pets and farm animals.

Administration of a type I IFN, or other ligand, in pure form or in an appropriate pharmaceutical composition can be carried out via any of the accepted modes of administration. The type I IFN may be administered locally or systemically. Thus administration can, for example, be orally, nasally, parenterally, topically, transdermally, or rectally. The type I IFN may be administered as solid or semi-solid dosage forms, lyophilized powder, or liquid dosage forms, including for example, tablets, suppositories, pills, soft elastic and hard gelatin capsules, powders, solutions, suspensions, or aerosols, or the like, preferably in unit dosage forms suitable for simple administration of precise dosages. The pharmaceutical conditions will typically include a conventional pharmaceutical carrier or excipient and the type I IFN. The compositions may also include other medicinal agents, pharmaceutical agents, carriers, adjuvants, etc. For a brief review of present methods for drug delivery, see Langer, 1990, *Science* 249:1527–1533, which is incorporated herein by reference.

The preferred route of administration of the type I IFN is parenterally, using a convenient daily dosage regimen. For such parenteral administration for example, a pharmaceutically acceptable composition containing a human β-IFN may be formulated by methods disclosed in U.S. Pat. Nos. 4,462,940, 4,588,585 and 4,992,271.

By "therapeutically effective amount", as used herein, is meant the quantity of a type I IFN sufficient to induce anti-proliferative effects in the target cell population. Amounts effective for this use will, of course, depend on the condition being treated and the weight and general state of the subject. Various considerations are described, e.g., in Gilman et al. (eds.) (1990) *Goodman and Gilman 's: The Pharmacological Bases of Therapeutics,* 8th ed., Pergamon Press; and *Remington 's Pharmaceutical Sciences,* 17th ed. (1990), Mack Publishing Co., Easton, Pa., each of which is herein incorporated by reference.

A therapeutically effective dose of a type I β-IFN in a human is typically, for example, about 0.05 mg Betaseron to about 0.25 mg Betaseron, administered subcutaneously, every other day. Therapeutically effective amounts of other interferon products, including other β-IFN products, may be determined routinely by one of skill in the art.

It is also contemplated as part of this invention that a gene encoding an IFNAR2c polypeptide will be delivered to the target cell population in conjunction with gene encoding a type I IFN. The IFNAR2c gene and the type I IFN gene may be delivered to the same cells or different cells of the target population. The IFNAR2c gene may delivered in the same composition and/or the same vector as the type I IFN gene. For example, the type I IFN gene and the IFNAR2c gene may be delivered as part of the same viral vector, for example, an adenovirus vector. Additionally, it is also contemplated as part of this invention that the IFN gene may be delivered to cells that are adjacent to cells of the target population. Additionally, type I IFN may be delivered to the target cells by the implantation of cells expressing type I IFN in or near the target cell population.

Figure 1:
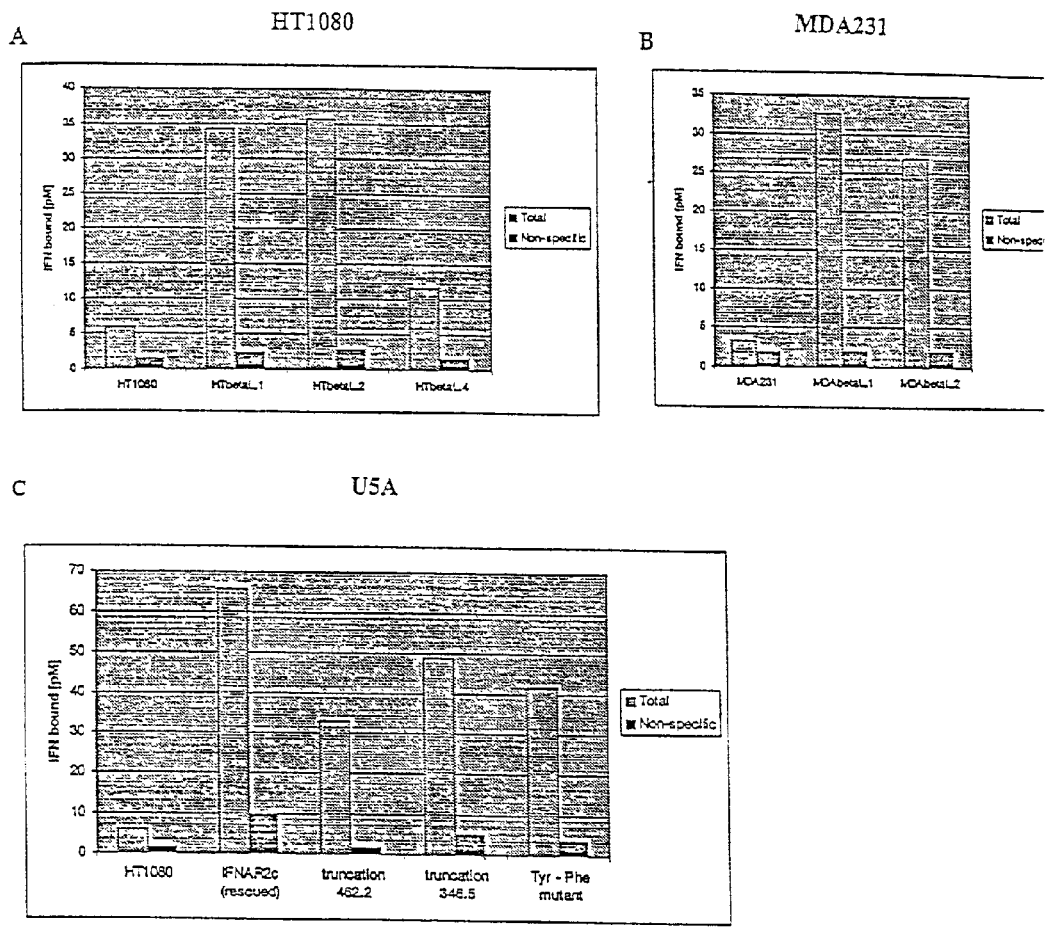
FIG. 1 is a series of histograms showing that cells transfected with the IFNAR2c gene express elevated levels of high affinity type I IFN receptors. Data represents the average of three separate points and standard errors are less than 10 percent of the average. Non-specific binding was measured in the presence of a 100-fold excess of unlabeled IFN. Panel A shows results obtained with transfected HT1080 cells. Panel B shows results obtained with transfected MDA231 cells. Panel C shows results obtained with U5A cells, which do not express IFNAR2c, including cells transfected with truncation mutants of the IFNAR2c gene.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius; and unless otherwise indicated, all parts and percentages are by weight.

The entire disclosure of all patents, patent applications, and publications, cited above or below are hereby incorporated by reference.

EXAMPLES

Example 1

Cells transfected with an IFNAR2c gene express elevated levels of high affinity type I IFN receptors.

Three cell lines transfected with IFNAR2c genes were evaluated for expression of high affinity type I IFN receptors by ligand binding assays using a phosphorylated form of IFNα2. High affinity ligand binding has previously been demonstrated to occur only when both IFNAR1 and IFNAR2c are expressed on the cell surface (Russell-Harde et al., 1995, *J. Biol. Chem.* 270:26033–26036). Therefore, ligand binding was used to confirm the expression of IFNAR2c receptor protein on the surface of cell lines transfected with IFNAR2c genes. The cell lines employed were as follows:

(i) HT1080 cells. A human lung fibrosarcoma cell line (ATCC No. CCL-121).
(ii) U5A cells. U5A cells are derived from HT1080 and are HT1080 cells that were selected for lack of IFNAR2c protein expression. U5A cells lack of the ability to respond to type I IFN (Pellegrini, et al., 1989, *Mol. Cell. Biol.* 9:4605–4612; Lutfalla et al., 1996, *EMBO J.* 14:5100–5108.
(iii) MDA231 cells. A human breast epithelial adenocarcinoma cell line (ATCC No. HTB-26).

HT1080 and MDA231 cell lines were purchased from the American Type Tissue Culture (ATCC), and all cell lines were grown at 37° C. in 5% $CO_2$.

Cells were transfected using Superfect (Qiagen Inc.), with expression plasmids containing full-length or mutant forms of human IFNAR2c. Plasmids containing genes encoding IFNAR2c truncation mutations or a tyrosine to phenylalanine mutation were constructed as previously described (Domanski et al., 1997, *J. Biol. Chem.* 272:26388–26393; Nadeau et al., 1999, *J. Biol. Chem.* 274:4045–4052). Stable transfected cell lines were selected in G418 (1.0 mg/ml). After selection, individual clones were picked and expanded, and integration of the IFNAR2c gene was confirmed by PCR analysis using intron spanning primers specific for IFNAR2c cDNA. Positive clones were further expanded and tested for their ability to bind type I IFN.

Ligand binding assays were performed as essentially described in Croze et al., 1996, *J. Biol. Chem.* 271:33165–33168. IFNα with a specific activity $3.0 \times 10^8$ IU/mg was obtained from PeproTech Inc. (Rocky Hill, N.J.) and the IFNα2 ligand was phosphorylated to a specific activity of 60–62 µCi/µg as previously described (Croze et al., 1996, *J. Biol. Chem.* 271:33165–33168). Ligand binding was analyzed by the addition of phosphorylated IFNα2 (at a concentration of 176 pM) to 200,000 cells for ninety minutes. Non-specific binding was determined by adding 100-fold excess of unlabeled IFNα2. Binding data were analyzed by Scatchard analysis.

Parental HT1080 cells bound IFNα2 with relatively high affinity (Kd~290 pM) and 9,000 receptor cites per cell were measured by Scatchard analysis. Three stable clones of HT1080 cells transfected with the wild-type IFNAR2c gene (HTbetaL.1, HTbetaL.2, and HTbetaL.4) were analyzed for IFNα2 binding. Two of the clones, HTbetaL.1 and HTbetaL.2, bound ~8-fold more ligand (34–37 pM bound) than parental HT1080 cells, whereas the third clone (HTbetaL.4) bound approximately two-fold more ligand (11–12 pM bound) than parental HT1080 cells (FIG. 1, Panel A).

Cells of the human breast adenocarcinoma cell line MDA231 were also transfected with a wild-type IFNAR2c gene. Two stable clones, MDAbetaL.1 and MDAbetaL.2, were analyzed for IFNα2 binding. The parental MDA231 cell line bound relatively low levels of IFNα2 (2–3 pM). Each of the transfected clones bound approximately ten-fold more IFNα2 than the parental MDA231 cell line (FIG. 1, Panel B).

U5A cells, which do not express the IFNAR2c receptor protein, were transfected with a wild-type IFNAR2c gene and four mutated genes, including three truncation mutants (R2.462, R2.417, R2.346) and a full tyrosine to phenylalanine substitution mutation (R2.Y-F) (a substitution of tyrosines at positions 269, 306, 316, 318, 337, 411 and 512 of SEQ ID NO. 3 with phenylalanine). U5A cells transfected with a wild-type IFNAR2c gene bound 13-fold more IFN than the parental HT1080 cells (FIG. 1, Panel C). Stable clones expressing the either the R2.462 or the R2.346 truncation mutation, or the (R2.Y-F) deletion mutation, bound IFNα2 at levels 5 to 10-fold greater than HT1080 cells (FIG. 1, Panel C). Stable clones expressing the R2.417 truncation mutation bound IFNα2 at approximately the same level as HT1080 cells (~9000 binding sites).

Example 2

Enhancing the sensitivity of U5A and HT 1080 cells to the anti-proliferative effects of IFNβ1b by transfecting the cells with an IFNAR2c gene.

U5A cells that were transfected with wild-type and mutant IFNAR2c genes were tested for sensitivity to the anti-proliferative effects of IFNβ1b in comparison to U5A cells. HT1080 cells that were transfected with a wild-type IFNAR2c gene were also tested for sensitivity to the anti-proliferative effects of IFNβ and IFNα in comparison to HT1080 cells. Cells were tested for sensitivity to the anti-proliferative effects of IFNβ1b using a thymidine incorporation assay.

Cells were seeded in 24-well culture plates at a density of $2 \times 10^4$ cells/well, 1 ml/well, and incubated with human IFNβ1b at a concentration of 1000 IU/ml for 24 hours. Human IFNβ1b (specific activity $2.5 \times 10^7$ IU/mg) was produced as described in (Russell-Harde, 1995, *J. Interferon Cytokine Res.* 15:31–37). At time zero, complete media containing tritiated thymidine ([methyl-$^3$H]thymidine, specific activity=40–60 Ci/mmol, Amersham Life Sciences) was added. Tritiated thymidine incorporation was measured after ten hours by the following method. Cells were washed with phosphate-buffered saline, followed by 10% trichloroacetic acid (TCA), and then 100% ethanol. Prior to the determination of the incorporation of radioactivity, cells were solubilized in 1 M potassium hydroxide and the solubilized cells were mixed with Ecolume scintillation fluid for measurement of tritiated thymidine incorporation.

Figure 2:
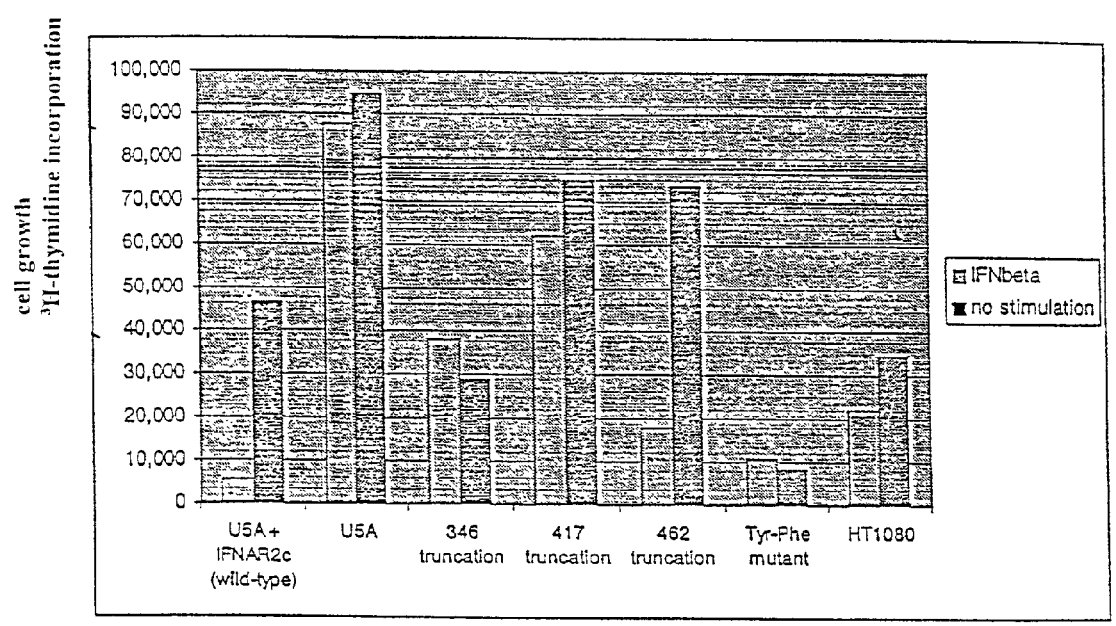
FIG. 2 is a histogram showing that U5A cells that were rescued by transfection with a functional IFNAR2c gene are extremely sensitive to the anti-proliferative activities of IFNβ1b in comparison to untransfected HT1080 cells. Data represents the average of three separate points and standard deviations were less than 15 percent of the average.

U5A cells that were transfected with the wild-type IFNAR2c gene were extremely sensitive to the anti-proliferative activities of IFNβ1b whereas U5A cells were not (FIG. 2). U5A cells that were transfected with a mutant IFNAR2c gene that encodes a protein truncated at residue 462 were also sensitive to the anti-proliferative effects of IFNβ1b. Two other truncation mutants, R2.417 and R2.246, and the R2.Y-F mutant (described in Example 1 above) were unresponsive to type I IFN. Therefore, truncation of the IFNAR2c receptor past residue 417 or removal of all the tyrosines present in the intracellular region of IFNAR2c (the R2.Y-F mutant) renders cells containing the two type I IFN receptor proteins insensitive to the anti-proliferative effects of type I IFNs. However, removal of the distal fifty-three residues (R2.462) of the IFNAR2c protein apparently has no effect on the receptor mediated anti-proliferative effects of type I IFNs. HT1080 cells expressing normal levels of the IFNAR2c receptor protein are only weakly sensitive to the anti-proliferative activities of IFNβ1b.

TABLE I

|  | Anti-proliferation | TUNEL apoptosis | Cell death |
|---|---|---|---|
| HT1080 (parental) | +/− | − | − |
| HTbetaL.2 | +++ | +++ | +++ |
| MDA231 (parental) | +/− | +/− | − |
| MDAbetaL.1 | ND | +++ | +++ |
| MDAbetaL.2 | ND | +++ | +++ |
| U5A + IFNAR2c (wild-type) | +++ | ND | +++ |
| 462 truncation | +++ | ND | +++ |
| 356 truncation | − | ND | ND |
| Tyr-Phe mutant | − | ND | − |

1. Anti-proliferation was measured by thymidine incorporation assay.
2. Cell death was measured by visual inspection as described in Example 4 below.
3. Apoptosis was measured by TUNEL assay, as described in Example 5 below.

Example 3

IFNAR2c transfected HT1080 cells expressing enhanced levels of IFNAR2c were sensitive to the effects of both type I IFNβ and type I IFNα.

Figure 3:
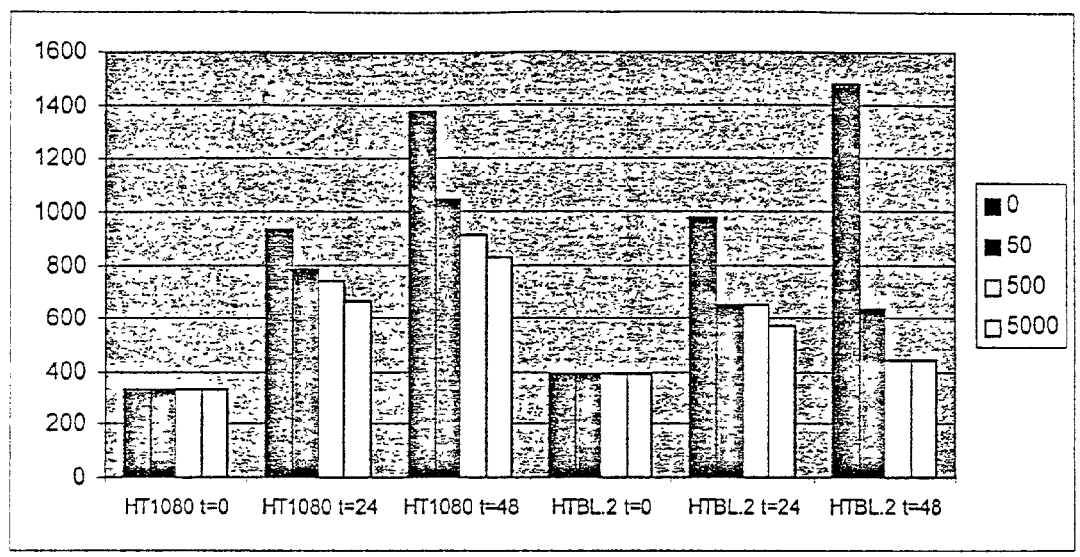
FIG. 3 is a histogram showing that HT1080 cells and HT1080 cells transfected with the IFNAR2c gene (HTbetaL.2) were sensitive to both incubation times with IFNβ1b and concentrations of IFNβ1b, although HTbetaL.2 cells showed enhanced sensitivity.

The effects of varying incubation times and concentrations of IFNβ1b on HT 1080 cells and HT 1080 cells transfected with a wild-type IFNAR2c gene (HTbetaL.2 cells) were compared using an Alamar Blue™ assay (Biosource #DAL 1100) to measure mitochondrial activity. Cells were plated at subconfluent density in 6-well dishes and were incubated with 0, 50, 500 or 5000 IU/ml of IFNβ1b for 0, 24 or 48 hours. At the various time points, Alamar Blue reagent was added to cells (1:10 dilution) and incubated on cells for 30 minutes. At 30 minutes, reduced/fluorescent Alamar Blue was detected with fluorescent plate reader. Both HT1080 cells and HTbetaL.2 cells exhibited dose- and time-dependent responses to IFNβ1b (FIG. 3). However, in contrast to HT1080 cells, HTbetaL.2 cells do not continue to grow from 24 to 48 hours. Although the proliferative rate of HT1080 cells is reduced upon IFNβ1b treatment, cell number continues to increase. In contrast, HTbetaL.2 cells actually decrease in cell number over time. This decrease is presumably due to apoptotic cell death induced in HTbetaL.2 cells and not in HT1080 cells.

Figure 4:
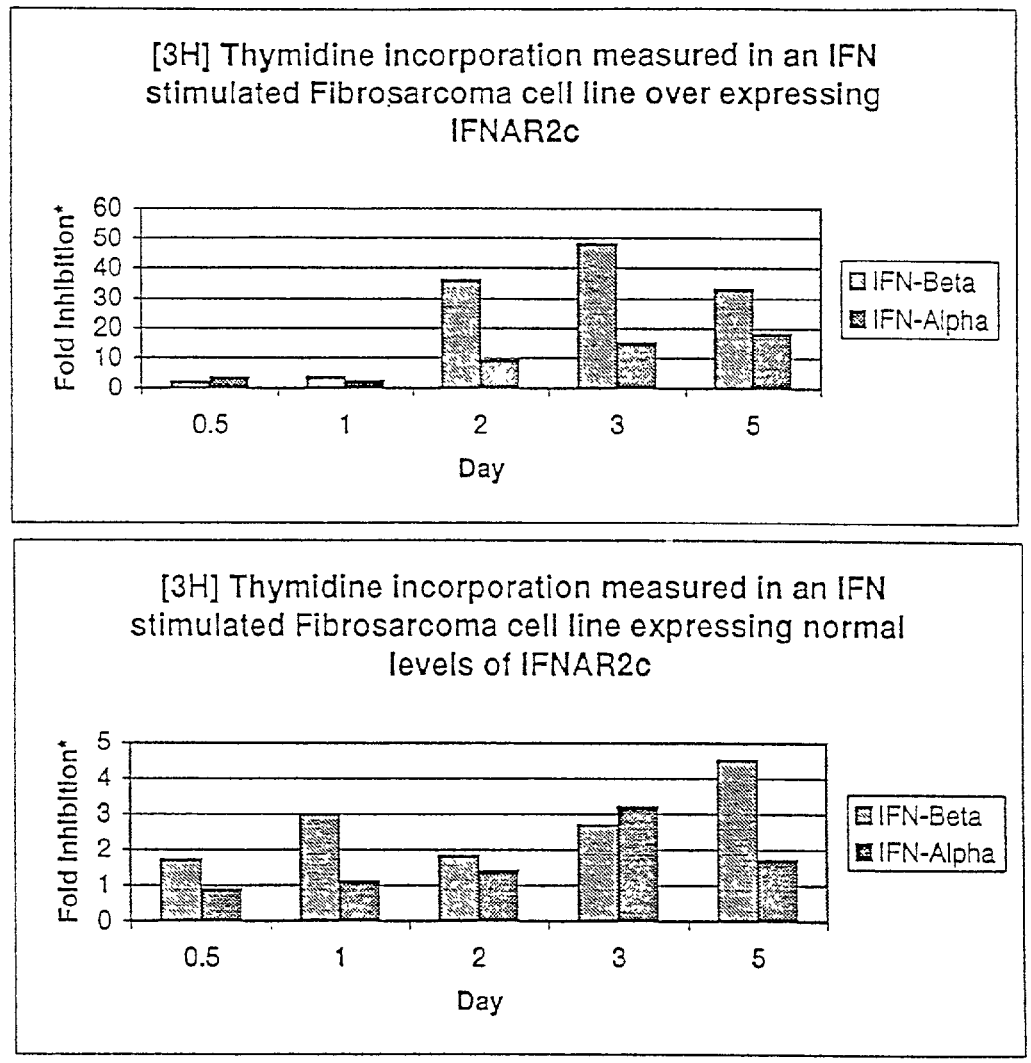
FIG. 4 is a histogram showing a comparison of the anti-growth effects of 5000 International Units ("IU")/ml of human IFNβ1b (Betaseron) or human IFNα2 on HT1080 cells and HT1080 cells transfected with the IFNAR2c gene, using a thymidine incorporation assay. Data is expressed as fold inhibition of cell growth.

A comparison of the anti-growth effects of both IFNβ and IFNα on HT1080 cells transfected with the IFNAR2c gene was conducted using a thymidine incorporation assay, described in Example 2 above, using 5000 IU/ml for both human IFNβ1b (Betaseron) and human IFNα2 (FIG. 4). This comparison demonstrated that both of the IFNs tested had anti-growth effects on the transfected cells.

Figure 5:
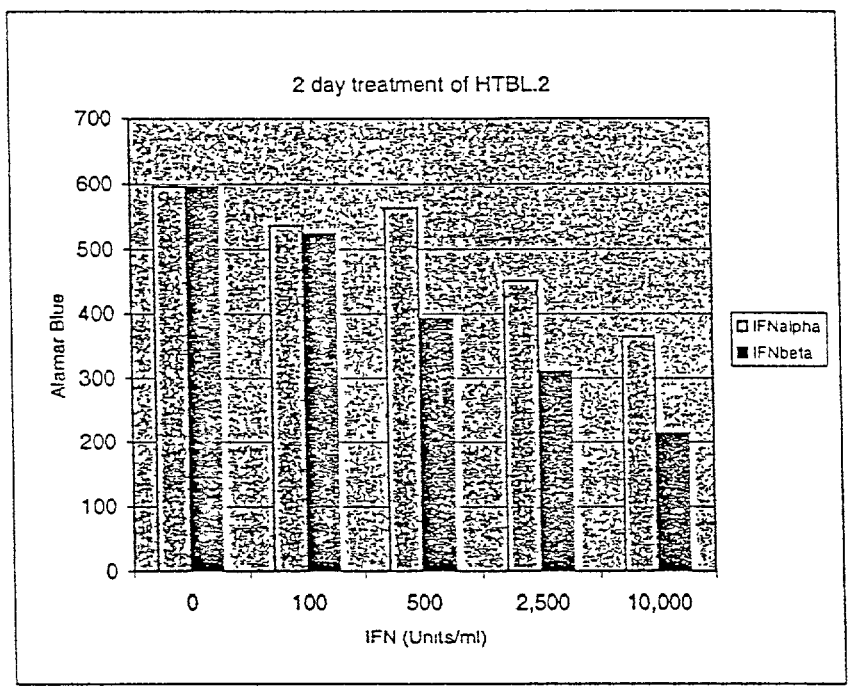
FIG. 5 is a histogram showing a comparison of the anti-growth effects of IFNβ1b and IFNα2 on HT1080 cells transfected with the IFNAR2c gene using an Alamar Blue assay.

A comparison of the anti-growth effects of varying concentrations of both human IFNβ1b and IFNα2 on HT1080 cells transfected with the IFNAR2c gene (HTbetaL.2) was also conducted using an Alamar Blue assay (FIG. 5). This comparison also demonstrated that IFNβ had a greater anti-growth effect than IFNα, and that this difference in effect between the two IFNs was more pronounced at higher concentrations of IFN.

Example 4

IFNAR2c transfected HT1080 and MDA231 cells were much more sensitive to the anti-proliferative effects of type I IFNs than the parental cell lines.

Figure 6:
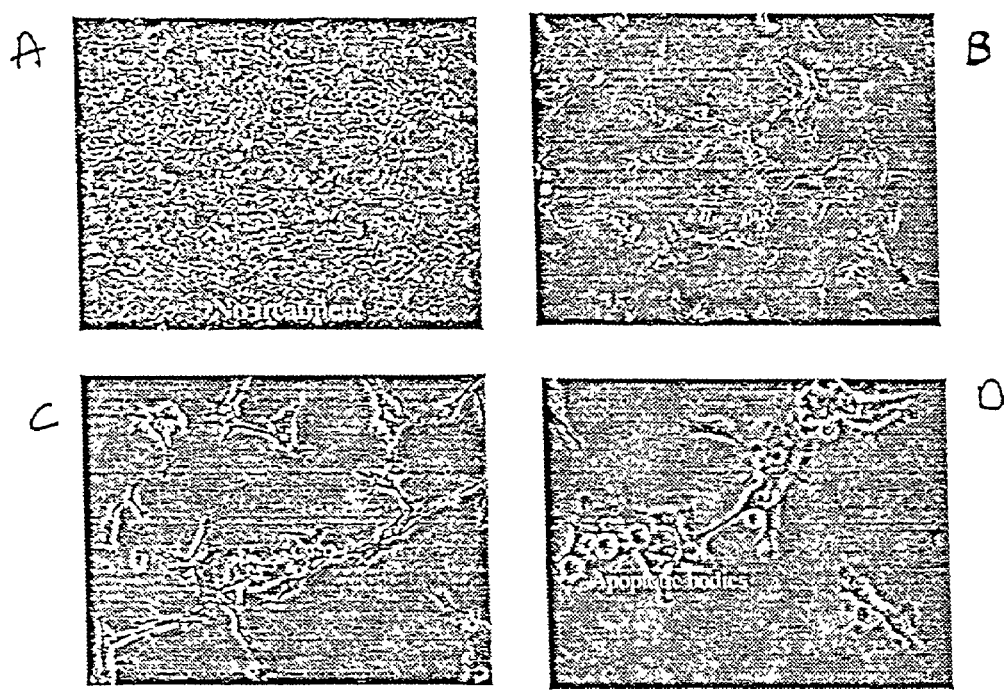
FIG. 6 shows photographic images of IFNAR2c transfected HT1080 (HTbetaL.2) cells after treatment of the cells with IFNβ1b. Panels A through D are as follows: Panel A, untreated cells (10× magnification); Panel B, treated cells (10× magnification); Panel C, treated cells (20× magnification); and Panel D, treated cells (40× magnification). Cells were treated with 500 IU/ml of IFNβ1b.

HT1080 cells are epithelial-like cells derived from a human fibrosarcoma. A stable transfected cell line derived from HT1080 (HTbetaL.2), which expressed enhanced levels of IFNAR2c, was examined for morphological changes after treatment with IFNβ1b (Table I). The cells were plated in a 6-well dish and were then treated with IFNβ1b at a concentration of 500 IU/ml. After two days, untreated cells had formed a confluent carpet of cells (FIG. 6, Panel A). IFNβ1b treated cells had not grown, and less cells were apparent after treatment than before (FIG. 6, Panel B). At higher magnifications, the morphology of the treated cells indicated that the cells were undergoing apoptosis (FIG. 6, Panel C (20×) and Panel D (40×)). Treated cells appeared to be shedding remnants of cell proteins and DNA in spherical "apoptotic bodies". HT1080 cells were not as severely affected by treatment with IFNβ1b as HTbetaL.2 cells, and apoptotic bodies were not observed in IFNβ1b treated HT1080 cells (FIG. 6, Panel B).

Figure 7:
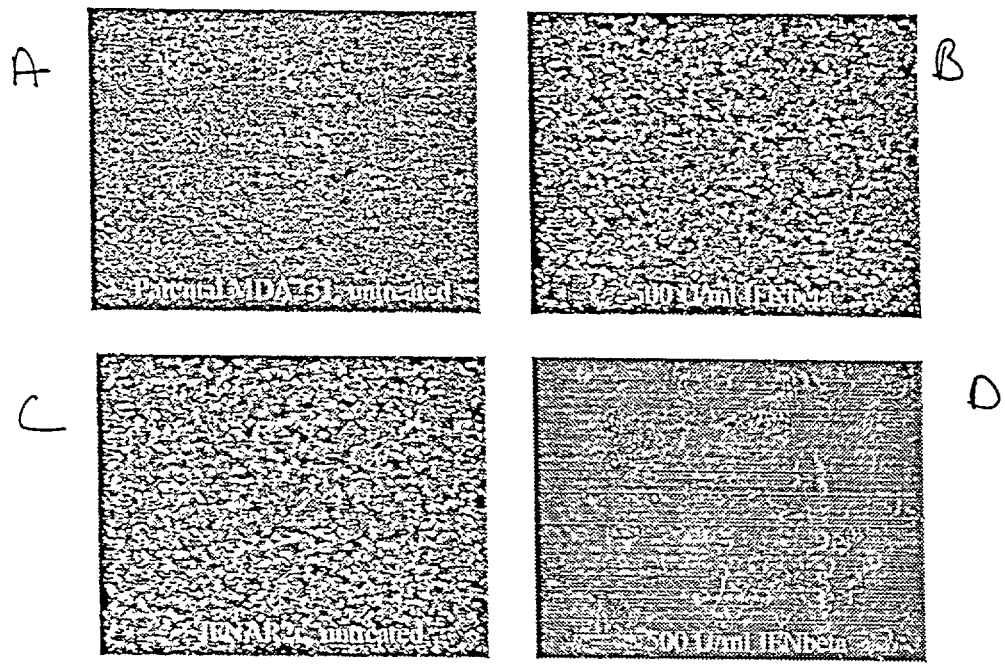
FIG. 7 shows photographic images of IFNAR2c transfected MDA231 cells after treatment of the cells with IFNβ1b. Panels A and B show untreated and treated parental MDA231 cells, respectively, at 10× magnification. Panels C and D show treated and untreated IFNAR2c transfected MDA231 cells, respectively, at 10× magnification. Cells were treated with 500 IU/ml of IFNβ1b.

Two stable transfected cell lines derived from MDA231 (MDAbetaL. 1 and MDAbetaL.2), which expressed enhanced levels of IFNAR2c, were examined for morphological changes after treatment with IFNβ1b (Table I). Cells were treated with IFNβ1b at a concentration of 500 IU/ml for three days before observation. The growth of parental MDA231 cells was only slightly impaired by treatment with IFNβ1b, as shown in FIG. 7, Panel A (untreated parental cells) and Panel B (treated parental cells). In contrast, MDAbetaL.2 cells were drastically inhibited in their growth when treated with 500 IU/ml IFNβ1b, as shown in FIG. 7, Panel C (untreated cells) and Panel D (treated cells). Like HT1080 cells that expressed enhanced levels of IFNAR2c, MDAbetaL.2 cells also appeared morphologically to undergo apoptosis when treated with IFNβ1b. Morphological changes were more difficult to assess in MDA231 cells than in HT1080 cells because normal MDA231 cells tend to appear rounded in shape, whereas HT1080 cells normally grow as flat triangles. However, enhanced apoptotic effects were observed in MDAbetaL.2 cells upon treatment with type I IFNs.

Example 5

HT1080 and MDA231 cells expressing enhanced levels of IFNAR2c protein were examined by TUNEL assay to confirm that the cells undergo apoptosis after treatment with IFNβ1b.

Apoptosis was measured in treated cells using a TdT-mediated dUTP nick end labeling (TUNEL) assay to label fragmented nuclear DNA, which is indicative of apoptosis (In Situ Cell Death Detection Kit, Boehringer Mannheim). In the TUNEL assay, fluorescent FITC labeled UTP nucleotides were transferred to the ends of fragmented DNA generated that is generated in the nuclei of cells undergoing apoptosis. Apoptotic cells stain bright green under a fluorescent microscope. After four days of IFN treatment, cells in 6-well cell culture plates were fixed for one hour at ambient temperature in 1×PBS containing 4% paraformaldehyde. Cells were then treated for one hour at ambient temperature with 0.3% $H_2O_2$ in methanol. Cells were then permeabilized for thirty minutes at ambient temperature in 0.3% Triton-X100 in PBS and were then washed, two times, with PBS. Fixed and permeabilized cells were dried, and cells fields were circled with a PAP pen (Biogenex). Apoptotic nuclei were then enzymatically labeled with the fluorescent label (FITC) as follows. Cells were incubated for forty-five minutes at 37° C. with 100 µl staining reagent from Boebringer Mannheim (450 µl Label Solution+50 µl enzyme solution). Stained cells were washed twice with PBS and were then imaged under a fluorescent microscope.

Figure 8:
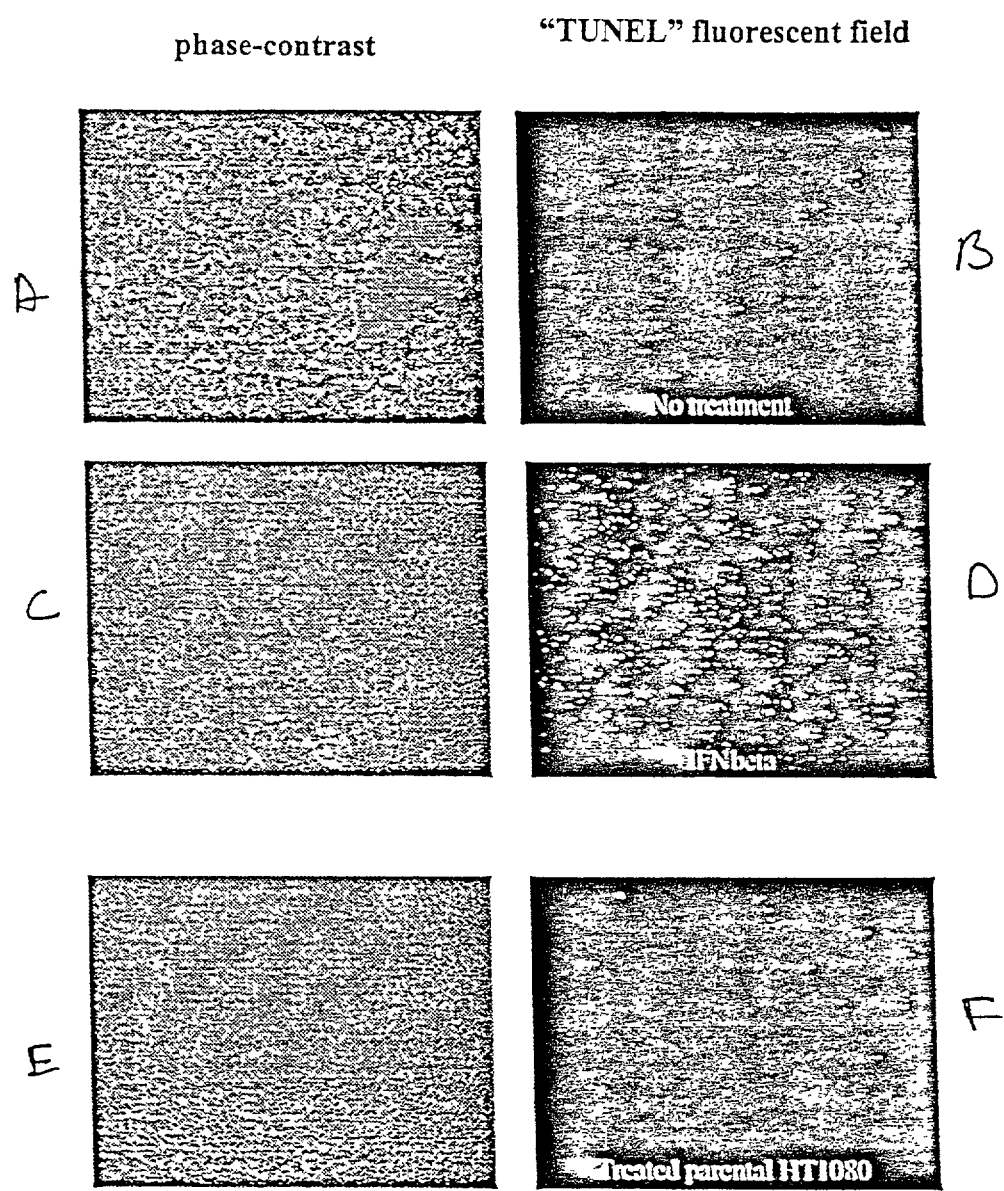
FIG. 8 is a series of microscopic images that show the results of an apoptosis assay (TUNEL assay) of the effects of IFNβ1b treatment of HT1080 cells that were transfected with a gene encoding the IFNAR2c receptor protein (HTbetaL.2 cells). Panels A–D are as follows: Panels A and B, untreated HTbetaL.2 cells, brightfield view and fluorescent microscope view, respectively; Panels C and D, IFNβ1b treated HTbetaL.2 cells, brightfield view and fluorescent microscope view, respectively; Panels E and F, parental HT1080 cells, brightfield view and fluorescent microscope view, respectively. Brightfield images Panels A, C, and E represent greater than 80% confluent cell layer. FITC labeled nucleotides were used to label DNA fragments characteristic of apoptotic cells (Panels B, D, and F). Cells were treated with 500 IU/ml of IFNβ1b. Magnification for Panels A–F was 10×.

Untreated transfected cells showed a limited number of TUNEL positive nuclei (FIG. 8: Panel A, brightfield view; Panel B, fluorescent microscope). Transfected cells that were treated with IFNβ1b showed a carpet of green TUNEL positive nuclei indicating a large fraction of cells were in the final stages of apoptosis (FIG. 8: Panel C, brightfield view; Panel D, fluorescent microscope). The small fraction of TUNEL positive cells in untreated cells may reflect endogenous production of low levels of type I IFN. HT1080 parental cells showed absolutely no signs of apoptosis after IFNβ1b treatment, indicated by a complete lack of TUNEL positive nuclei (FIG. 8: Panel E, brightfield view; Panel F, fluorescent microscope).

Figure 9:
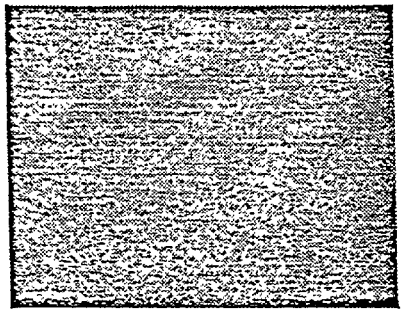
FIG. 9 is a series of microscopic images that show the results of an apoptosis assay (TUNEL assay) of the effects of IFNβ1b treatment of MDA231 cells that were transfected with a gene encoding the IFNAR2c receptor protein (MDAbetaL.2 cells). Panels A–F are as follows: Panels A and B, untreated MDAbetaL.2 cells, brightfield view and fluorescent microscope view, respectively; Panels C and D, IFNβ1b treated MDAbetaL.2 cells, brightfield view and fluorescent microscope view, respectively; Panels E and F, parental MDA231 cells, brightfield view and fluorescent microscope view, respectively. Brightfield images Panels A, C, and E represent greater than 80% confluent cell layer. FITC labeled nucleotides were used to label DNA fragments in apoptotic cells (Panels B, D, and F). Cells were treated with 500 IU/ml of IFNβ1b. Magnification for Panels A–F was 10×.
Figure 9:
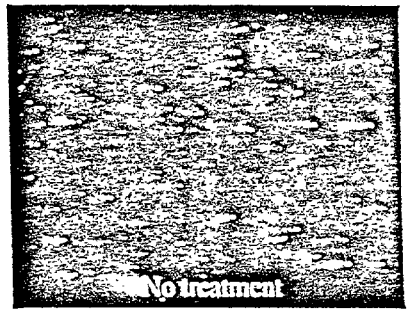
Figure 9:
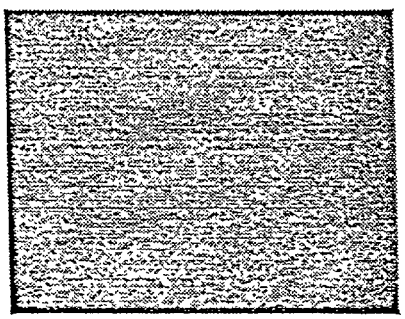
Figure 9:
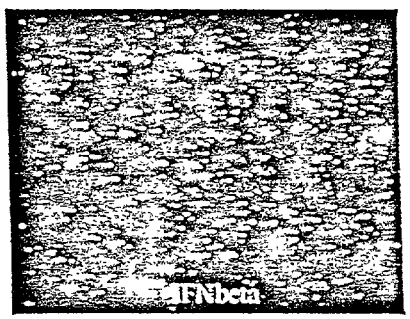
Figure 9:
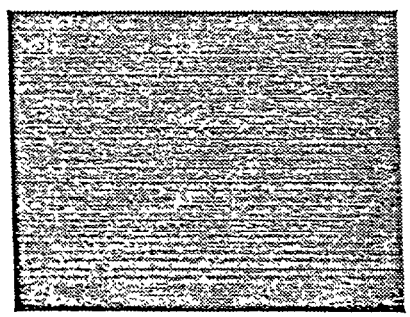
Figure 9:
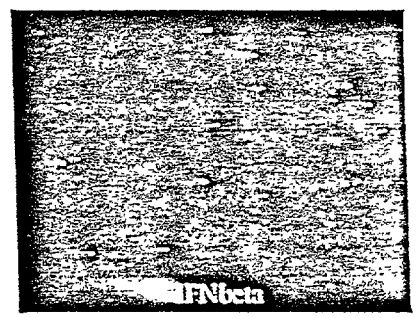
Figure 10:
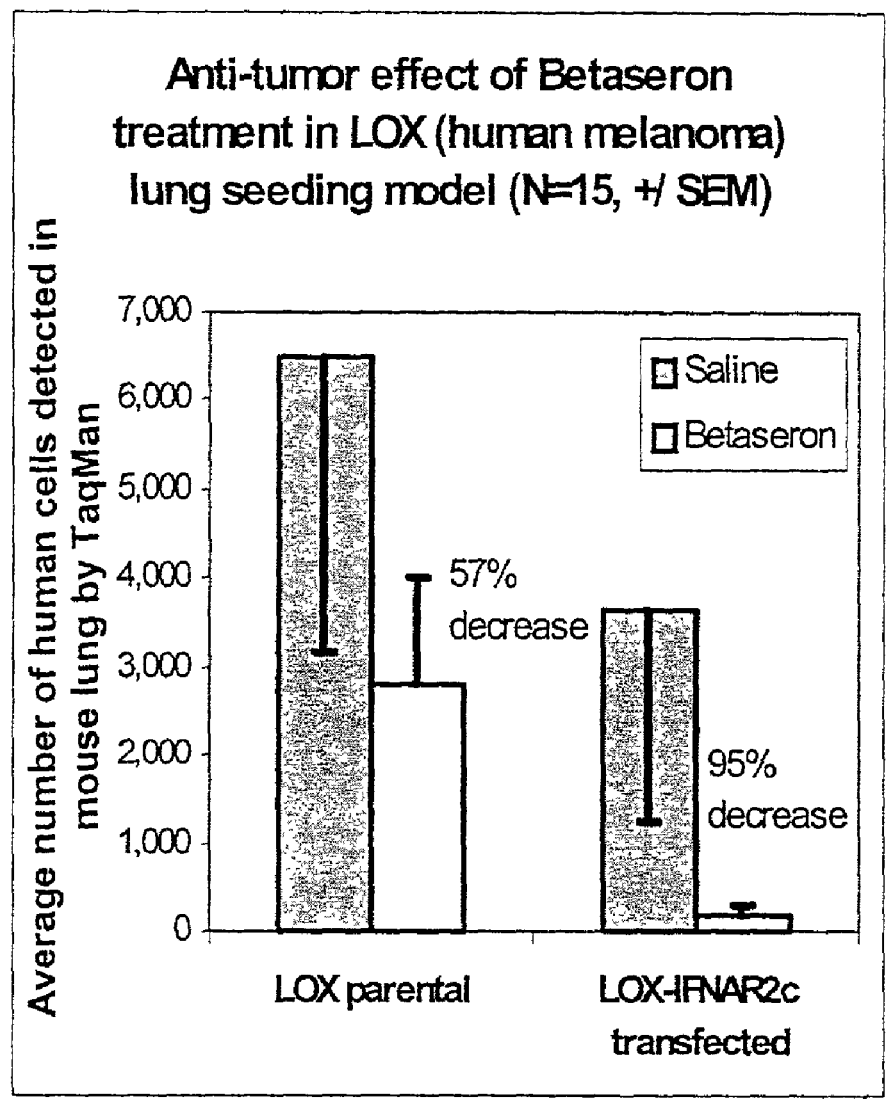
FIG. 10 is a histogram that shows the in vivo anti-growth activity of IFNβ1b (Betaseron) on LOX human melanoma cells and on LOX-IFNAR2c cells (LOX cells transfected with a functional IFNAR2c gene) using a mouse lung seeding model. The LOX-IFNAR2c cells showed enhanced sensitivity to 200 μg Betaseron given intraperitioneally every other day.

The results obtained with TUNEL assay of MDA231 cells were similar to those obtained with HT1080 cells. Untreated, transfected MDA231 cells (MDAbetaL.2) showed a limited number of TUNEL positive nuclei (FIG. 9: Panel A, brightfield view; Panel B, fluorescent microscope). Transfected MDA231 cells (MDAbetaL.2) that were treated with IFNβ1b showed a carpet of green TUNEL positive nuclei indicating a large fraction of cells were in the final stages of apoptosis (FIG. 9: Panel C, brightfield view; Panel D, fluorescent microscope). Parental MDA231 cells showed only minor signs of apoptosis when treated with 500 IU/ml of IFNβ1b for four days (FIG. 8: Panel C, brightfield view; Panel D, fluorescent microscope). The fraction of TUNEL positive cells in untreated MDAbetaL.2 cells may reflect endogenous production of low levels of type I IFN.

Example 6

A human tumor cell line transfected with IFNAR2c was more sensitive to the in vivo anti-growth activity of IFNβ1b than the parental cell line.

Injection of LOX human melanoma cells into the tail vein of nude mice will result in the development of defined tumors in the lungs at four weeks post-injection. This model was employed to assess the effectiveness of IFNβ1b treatment of tumor cells that express enhanced levels of the IFNAR2c protein. Nude mice (15 per group) were injected with either parental LOX cells or LOX cells transfected with a gene encoding an IFNAR2c receptor protein. Every other day, starting on day 2 post-injection, mice were injected intraperitoneally with either 200 μg Betaseron or an equivalent volume (200 μl) of saline. At 28 days post-injection, the mice were sacrificed and their lungs were removed and homogenized. DNA was extracted by proteinase K digestion followed by purification over a Qiagen column. The amount of human DNA in the lungs, an indirect measure of the number of LOX parental or LOX-IFNAR2c tumor cells, was quantified by TaqMan® PCR, using primers and probes that are specific for the human CCR5 gene. A standard curve was prepared using purified human genomic DNA.

Both LOX parental and LOX-IFNAR2c cells were sensitive to the anti-growth activity of systemic Betaseron in vivo, and LOX cells transfected with IFNAR2c displayed enhanced sensitivity.

Injection of MDA231 cells into the thigh muscle of nude mice will result in the development of defined tumors at two weeks post-injection. This model may be used to assess the effectiveness of IFNβ1b treatment of tumor cells that express enhanced levels of the IFNAR2c protein. Nude mice are injected with either parental MDA231 cells or MDA231 cells transfected with a gene encoding an IFNAR2c receptor protein. The effect of IFNβ1b administered systemically in inhibiting tumor proliferation in the injected mice is assessed by sacrificing the mice and measuring the size of the tumors.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A method for enhancing type I IFN growth inhibition of a human tumor target cell population possessing functional interferon alpha receptor 2c (IFNAR2c) polypeptide chains, said method comprises the steps of:
   (a) introducing an exogenous polynucleotide encoding a human IFNAR2c polypeptide chain directly into cells of said human tumor target cell population to produce modified target cells, wherein the modified target cells possess an increased number of functional IFNAR2c polypeptide chains on their cell surface as compared with unmodified target cells, and
   (b) contacting the modified target cells with a therapeutically effective amount of a human type I IFN, wherein the growth inhibition in the presence of the therapeutically effective amount of a human type I IFN for the modified target cells is enhanced as compared with unmodified target cells.

2. The method of claim 1, wherein the human type I IFN is a type I α-IFN, a type I β-IFN, or a type I ω-IFN.

3. The method of claim 1, wherein said exogenous polynucleotide is a viral vector encoding the human IFNAR2c polypeptide chain.

4. The method of claim 3, wherein the viral vector is a retroviral vector or an adenoviral vector.

5. The method of claim 1, wherein said exogenous polynucleotide is introduced directly into cells of said human tumor target cell population by electroporation.

6. The method of claim 1, wherein the growth inhibition is enhanced by at least 5%.

7. The method of claim 1, wherein the growth inhibition is enhanced by at least 10%.

8. The method of claim 3, wherein said viral vector further comprises a polynucleotide encoding a human type I IFN.

* * * * *